(12) United States Patent
Nutter (10) Patent No.: US 10,201,690 B2
(45) Date of Patent: Feb. 12, 2019

(54) WOUND INJECTOR APPARATUS

(71) Applicant: Robert Nutter, Reno, NV (US)

(72) Inventor: Robert Nutter, Reno, NV (US)

( * ) Notice: Subject to any disclaimer, the term of this patent is extended or adjusted under 35 U.S.C. 154(b) by 1165 days.

(21) Appl. No.: 14/302,283

(22) Filed: Jun. 11, 2014

(65) Prior Publication Data

US 2015/0025447 A1    Jan. 22, 2015

Related U.S. Application Data

(60) Provisional application No. 61/837,113, filed on Jun. 19, 2013.

(51) Int. Cl.
*A61M 35/00* (2006.01)
*A61M 39/24* (2006.01)

(52) U.S. Cl.
CPC .......... *A61M 35/003* (2013.01); *A61M 39/24* (2013.01); *A61M 2205/8218* (2013.01)

(58) Field of Classification Search
CPC .................... A61M 2205/8218; A61M 35/003
See application file for complete search history.

(56) References Cited

U.S. PATENT DOCUMENTS

| | | | | |
|---|---|---|---|---|
| 5,759,171 A * | 6/1998 | Coelho | ............ | A61B 17/00491 239/419.3 |
| 5,951,531 A * | 9/1999 | Ferdman | ................ | A61M 11/02 604/24 |
| 6,252,129 B1 * | 6/2001 | Coffee | .............. | A61F 13/00085 239/3 |
| 2002/0068905 A1 * | 6/2002 | Cowan | .............. | A61M 5/14546 604/181 |
| 2007/0123815 A1 * | 5/2007 | Mark | ................. | A61B 17/3468 604/22 |
| 2008/0004549 A1 * | 1/2008 | Anderson | ........... | A61M 1/0023 601/6 |
| 2010/0268177 A1 * | 10/2010 | Hall | ..................... | A61F 13/0203 604/313 |
| 2011/0202016 A1 * | 8/2011 | Zugates | ................ | A61L 24/043 604/290 |
| 2011/0251580 A1 * | 10/2011 | Greenhalgh | ........... | A61M 11/00 604/500 |
| 2012/0305669 A1 * | 12/2012 | Meron | ............. | A61B 17/00491 239/428 |
| 2013/0116641 A1 * | 5/2013 | Hicks | .................. | A61L 26/0085 604/319 |
| 2014/0161738 A1 * | 6/2014 | Goessl | ................ | A61L 26/0052 424/43 |
| 2014/0242064 A1 * | 8/2014 | Morriss | ................ | A61K 9/0043 424/94.67 |

\* cited by examiner

*Primary Examiner* — Susan Su
(74) *Attorney, Agent, or Firm* — Kerr IP Group, LLC (57) ABSTRACT

A wound injector apparatus is described. The wound injector includes a clotting factor, an expandable material, a thermal agent, a chamber, and a nozzle. At least one chamber houses the clotting factor, the expandable factor and the thermal agent. Additionally, at least one nozzle is configured to discharge at least one of the clotting factor, the expandable material, and the thermal agent.

18 Claims, 6 Drawing Sheets

WOUND INJECTOR APPARATUS

CROSS REFERENCE

The present patent application claims the benefit of provisional patent application No. 61/837,113, filed Jun. 19, 2013.

FIELD

The present invention relates to a wound injector apparatus. More particularly, the wound injector apparatus slows down the bleeding of a wound.

BACKGROUND

In emergency medicine, the "golden hour" refers to the time period lasting from minutes to several hours following a major multisystem trauma. It is widely believed that the victim's chances of survival are greatest if he or she receives definitive care within the first hour. The term "golden hour" refers to the U.S. military wartime experience, particularly in the Vietnam War. The golden hour can be summarized by the 3 R rule of Dr. Donald Trunkey, an academic trauma surgeon, i.e. "getting the right patient to the right place at the right time."

The "golden hour" not only relates to transporting the patient to a suitable facility for surgical intervention and/or treatment, but also to treating the patient immediately on scene or en route. Immediate treatment can make the difference in maximizing the patient's chances of survival.

In cases of severe trauma, uncontrolled bleeding is the leading cause of potentially preventable early in-hospital deaths. Therefore, there is a need for a system to stop or slow down traumatic bleeding that can be readily applied or used on scene or en route to a suitable facility.

SUMMARY

A wound injector apparatus is described. The wound injector includes a clotting factor, an expandable material, a thermal agent, a chamber, and a nozzle. At least one chamber houses the clotting factor, the expandable factor and the thermal agent. Additionally, at least one nozzle is configured to discharge the clotting factor, the expandable material, and the thermal agent.

In one illustrative embodiment, the wound injector further includes a propellant chamber and a propellant housed in the propellant chamber. In the illustrative embodiment, the propellant chamber is divided into a first propellant chamber, a second propellant chamber, and a third propellant chamber. The propellant includes a first propellant housed in the first propellant chamber and the first propellant is associated with the clotting factor. The propellant also includes a second propellant housed in the second propellant chamber and the second propellant is associated with the expandable material. The propellant further includes a third propellant housed in the third propellant chamber and the third propellant is associated with the thermal agent.

In the embodiments presented herein, the illustrative propellant includes at least one of $O_2$ $CO_2$ and $N_2$. The illustrative propellant may also function as a thermal agent.

In another illustrative embodiment, the wound injector includes a first chamber housing the clotting factor, a second chamber housing the expandable material, and a third chamber housing the thermal agent. This embodiment may further include a three-way valve controlling discharge from the first chamber, the second chamber and the third chamber.

Each of the embodiments may further include a selector switch for controlling the three-way valve that controls the discharge from the first chamber, the second chamber and the third chamber.

In the illustrative embodiments, the clotting factor includes at least one of thrombin, prothrombin, vitamin K, an adsorbent chemical, a hemostatic chemical and a fibrin glue.

Additionally, the wound injector may further include a sleeve that is configured to be used to apply direct pressure to a wound when filled with at least the expandable material. In the illustrative embodiment, the sleeve is composed of an elastomeric material.

In the illustrative embodiments, the expandable material is biocompatible and as the expandable material cures, the expandable material hardens.

The wound injector apparatus may also include an indicator configured to indicate a remaining amount of at least one of the clotting factor, the expandable material and the thermal agent.

In the illustrative embodiment, the at least one nozzle includes a first nozzle for discharging the clotting factor, a second nozzle for discharging the expandable material, and a third nozzle for discharging the thermal agent. Additionally, a diffuser may be attached to at least one nozzle.

Another illustrative embodiment includes a first container, a second container and a third container. The first container includes a first chamber housing the clotting factor, a first propellant chamber housing a first propellant, and a first nozzle for discharging the clotting factor. The second chamber includes a second chamber housing the expandable material, a second propellant chamber housing a second propellant, and a second nozzle for discharging the expandable material. The third container includes a third chamber housing the thermal agent, a third propellant chamber housing a third propellant, and a third nozzle for discharging the thermal agent. By way of example and not of limitation, the wound injector includes a fastener connecting the first container, the second container and the third container. Alternatively, an adhesive connect the first container, the second container and the third container.

DRAWINGS

The present invention will be more fully understood by reference to the following drawings which are for illustrative, not limiting, purposes.

DESCRIPTION

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the apparatus and methods described herein may vary as to configuration and as to details. Additionally, the methods may vary as to details, order of the actions, or other variations without departing from the illustrative method disclosed herein.

Embodiments of a wound injector apparatus enable the stopping and slow-down of bleeding of a wound during the golden hour. In particular, embodiments enable the performance of three operations: (1) applying a clotting factor to the wound to slow down the bleeding from the wound; (2) applying physical pressure to the wound; and (3) applying a "thermal" agent to further slow down bleeding.

Embodiments of the wound injector apparatus include a clotting factor, an expandable material, and a thermal agent. The wound injector apparatus can be packaged in a can, or in an alternative container including one or more chambers for the clotting factor, the expandable material, and the thermal agent. One or more of the active ingredients can be combined and housed within a single chamber if these ingredients are compatible and do not react with each other.

The clotting factor induces clotting near the wound or along the cavity wound. Clotting factors can include thrombin, prothrombin, and Vitamin K. However, it is to be understood that any suitable clotting factor which induces coagulation may be used. For example, alternative embodiments may also use fibrin glue, adsorbent chemicals, such as zeolites, and other hemostatic agents.

One or more clotting factors may be used to induce coagulation. By way of example and not of limitation, one embodiment of the wound injector may include one clotting factor, while another embodiment may include two or more clotting factors in order to induce faster coagulation. The clotting factors may be combined and housed within a single chamber (or in combination with one of the other active ingredients), or alternatively they may be housed within separate chambers.

The expandable material is used to apply physical pressure to the wound. The illustrative expandable material is biocompatible and non-toxic. In one embodiment, the expandable material may be a gas, a liquid, a semi-solid, foam, or a combination of any of these states. The expandable material also hardens as the expandable material cures, when applied to the wound. Depending on a number of factors, the expandable material can be applied directly to the wound or used to fill a sleeve which comes in contact with the wound.

From herein, "sleeve" will be used to refer to a material that comes in direct contact with the wound one side of the sleeve (not shown). The opposite side of the sleeve receives at least the expandable material. The sleeve prevents the expandable material from coming in contact with the wound and keeps the expandable material from being dispersed to areas beyond the wound. Thus, the sleeve enables controlled delivery of the expandable material, and optionally of the clotting factor and the thermal agent.

The sleeve may be composed of an elastomeric material. The elastomeric material receives the expandable material, resulting in internal pressure being applied to the wound, i.e. an "internal tourniquet." This differs from traditional tourniquets solutions where direct pressure is only applied from the outside of the wound. The elastomeric material can be made of latex or other suitable bio-compatible material.

In alternative embodiments, the sleeve may consist of a tube. The tube can be made of a bio-compatible elastomeric material, including silicone, rubber, latex, thermoplastic elastomers, and other such materials. The tube may be inserted into the wound cavity and filled with the expandable material. Depending on the wound, the tube may be inserted the wound cavity, and then filled with the expandable material. Alternatively, the tube may be inserted filled or partially-filled. The distal end of the tube may be closed to prevent the expandable material from exiting the tube while filling the tube.

The sleeve tube may be cut and sized to have a length that best fits the wound cavity. Tubes of differing diameters and flexibility may also be used for differently sized wounds. For example, a tube may be selected to be firm enough to be pushed into the wound cavity, yet flexible enough to collapse when passing through narrow portions of the wound cavity. If the tube is being used to apply pressure to the wound created by the path of a bullet, then the tube can be inserted through the wound opening, with the tube being flexible enough to collapse in portions where the diameter of the wound cavity is smaller.

The thermal agent provides a cold component to the wound. The thermal agent may be used as a curing compound for the clotting factor and the expandable material. The thermal agent can be biocompatible and not react with the clotting factor or the expandable material. The thermal agent may be $O_2$, $CO_2$, and $N_2$, among others. Alternatively, the thermal agent can be a bio-compatible chemical which creates an endothermic reaction when discharged into the wound.

The thermal agent can be applied directly to the wound. Alternatively, the thermal agent may be discharged or injected into the expandable material. Releasing the thermal agent through the expandable material enables the thermal agent to cool the expandable material, and consequently provide an indirect cold to the wound. This is beneficial when the thermal agent has the potential to freeze and damage the tissue surrounding the wound. The thermal agent may also be injected or discharged into the sleeve. Releasing the thermal agent into the sleeve provides controlled delivery of the thermal agent, and it shields the tissue surrounding the wound from damage due to exposure to extreme cold.

An illustrative wound injector may also include a propellant. The same propellant may be used for the clotting factor, the expandable material, and the thermal agent. Alternatively, a different propellant may be used for each of the clotting factor, the expandable material, and the thermal agent. A first propellant may also be used for two of the active ingredients of the injector, while a second propellant may be used for the third active ingredient of the injector. The propellant may also preserve the active ingredient.

The wound injector apparatus may be a disposable, one-time use device. In alternative embodiments, the wound injector may be used multiple times before having to be discarded. The wound injector apparatus may optionally include an indicator indicating the remaining level of the active ingredients in the container.

Figure 1A:
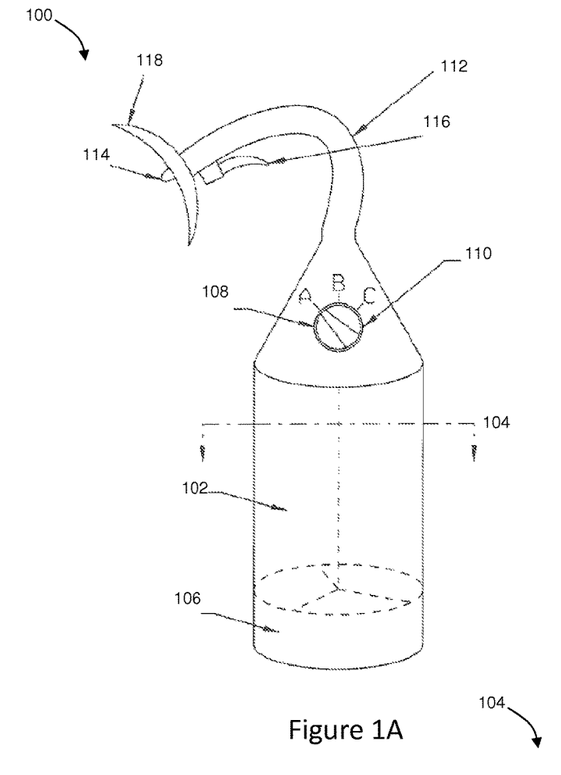
FIG. 1A shows a front view of a wound injector with a flexible neck.

FIG. 1A shows a front view of a wound injector apparatus 100 in accordance with an embodiment. The wound injector 100 includes a cylindrical body 102 including three chambers for the clotting factor, the expandable material, and the thermal agent. Propellant chamber 106 houses the propellant. A selector switch 108, including labels 110, enables the user to control the three-way valve for selecting which of the active ingredients to discharge. A flexible hose 112 connects the three-way valve to the nozzle 114. The flexible hose 112 enables the nozzle 114 to be oriented at a plurality of angles and positions. The flexible hose can be rigid enough to enable the hose to remain upright and in the user desired position. Alternatively, the flexible hose can consisting of a rubber tube allowing the user complete freedom to position and stretch the neck of the wound injector during use.

A trigger 116 allows for the discharge of the selected active ingredient. The trigger 116 is positioned adjacent to the nozzle 114 and behind an optional cover 118 surrounding nozzle 114. It is to be understood that the trigger 116 can be positioned anywhere along the flexible hose 112 or on the body of the wound injector 100. For example, the trigger 116 may be positioned adjacent to the sector 108. Alternatively, the selector 108 may serve both functions of selecting which of the active ingredients to discharge and also discharging the selected active ingredient. For instance, the selector 108 may be pushed down to trigger the discharge of the selected active ingredient.

The trigger 116 may also enable the controlled delivery of each active ingredient based on the pressure applied to the trigger 116. For example, based on the pressure applied, the wound injector can discharge the selected active ingredient at a high pressure or at a low pressure (for delicate wounds or wounds in delicate areas).

In one illustrative embodiment, a plurality of diffusers can be installed on the nozzle 114, enabling custom discharge of the various active ingredients. For instance, the diffuser may be cone-shaped, or it may consist of a rigid tube or a flexible tube (such as a Tygon tube). Cone and tube diffusers of various sizes and diameters can be used as needed depending on the wound and patient conditions. The diffuser installed on the nozzle 114 can be interchangeable, such that a first diffuser can be used for a first type of wound, while a second diffuser can be used for a second type of wound. Different diffusers may also be used for the application of the different active ingredients. For example, a first diffuser can be used for the clotting factor and the thermal agent, while a second diffuser can be used for the expandable material.

As noted above, the cover 118 of the nozzle 114 can either be fixed to the wound injector, or it may be removable. The cover 118 is shown as being substantially concave or cone shaped. However, it is to be understood that any cover which provides a degree of protection may also be used. Differently sized and shaped covers may be used for different types of wounds and/or for the application of the various active ingredients.

Figure 1B:
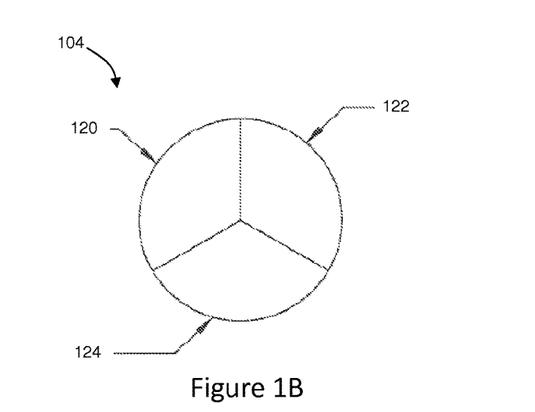
FIG. 1B shows a top view of the three chambers of the wound injector from FIG. 1A.

FIG. 1B illustrates a top view of sectional view 104, showing a first chamber 120 housing a clotting factor, a second chamber 122 housing an expandable material, and a third chamber 124 housing a thermal agent. While FIG. 1B illustrates the three chambers having substantially the same dimensions, in alternative embodiments the three chambers can be of differing sizes depending on the pressure and volume requirements of each active ingredient. For instance, if the expandable material requires a larger volume to hold the expandable material, then chamber 122 housing the expandable material can be made larger to accommodate the larger volume.

In an alternative embodiment, the clotting factor may be combined with the thermal agent and stored within a single chamber in the wound injector. In such an embodiment, the wound injector may include two chambers, with one chamber housing the combined clotting factor and thermal agent, and with a second chamber housing the expandable material.

In yet another embodiment, the clotting factor, the expandable material, and the thermal agent may be combined. In such an embodiment, the combined ingredients may be housed within a single chamber. It is to be understood that any of the active ingredients may be combined into one or more chambers as long as the combination of these active ingredients do not react with each other within the chambers.

In one embodiment, the three ingredients may be combined within a single chamber. One or more other chambers may also contain the combined ingredients of a clotting factor, an expandable material, and a thermal agent. Each chamber may then hold the equivalent of a single usage. The selector of the injector may then be used to switch from one chamber to the next after each use.

Figure 1C:
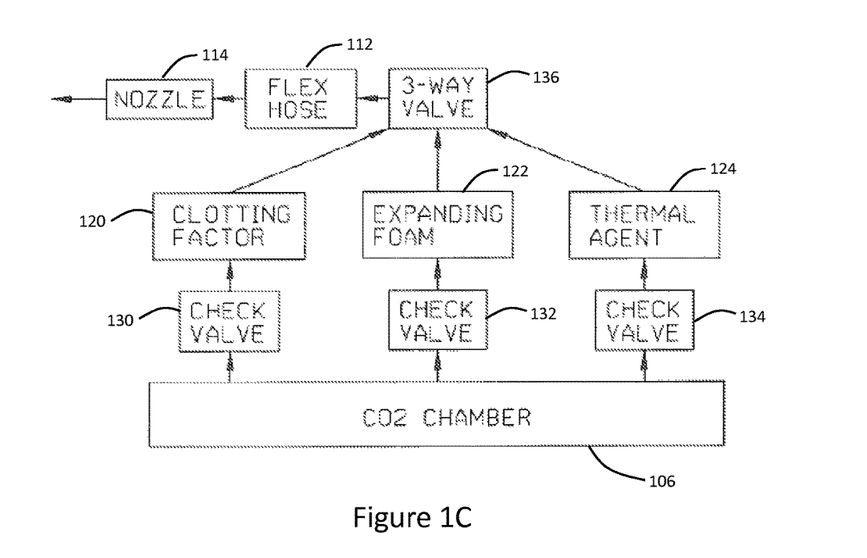
FIG. 1C illustrates a schematic diagram of the wound injector from FIG. 1A.

FIG. 1C shows a schematic diagram of the wound injector 100. Check valves 130, 132 and 134 allow the propellant from the propellant chamber 106 to flow into the clotting factor chamber 138, the expandable material chamber 140, and the thermal agent chamber 142 to force these active ingredients through nozzle 114. Three-way valve 136 is used to select which of the active ingredients is discharged. A flexible house 112 connects the three-way valve 135 to nozzle 114.

As noted above, while FIG. 1C illustrates only one propellant chamber, in alternative embodiments the wound injector can include two or more propellant chambers, with each propellant chamber housing a propellant associated at least one of the active ingredients. For example, a first propellant, housed in a first propellant chamber, may be associated with the clotting factor, while a second propellant, housed in a second propellant chamber, may be associated with the expandable material and the thermal agent.

Figure 2:
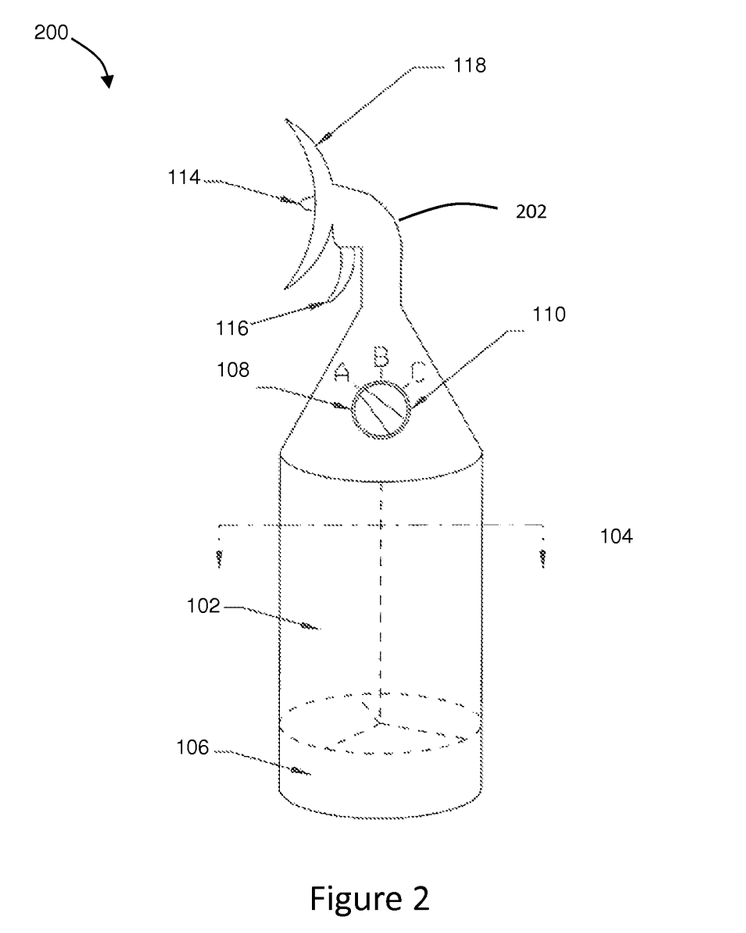
FIG. 2 illustrates a front view of a wound injector with an about 90 degree angle nozzle.
Figure 3:
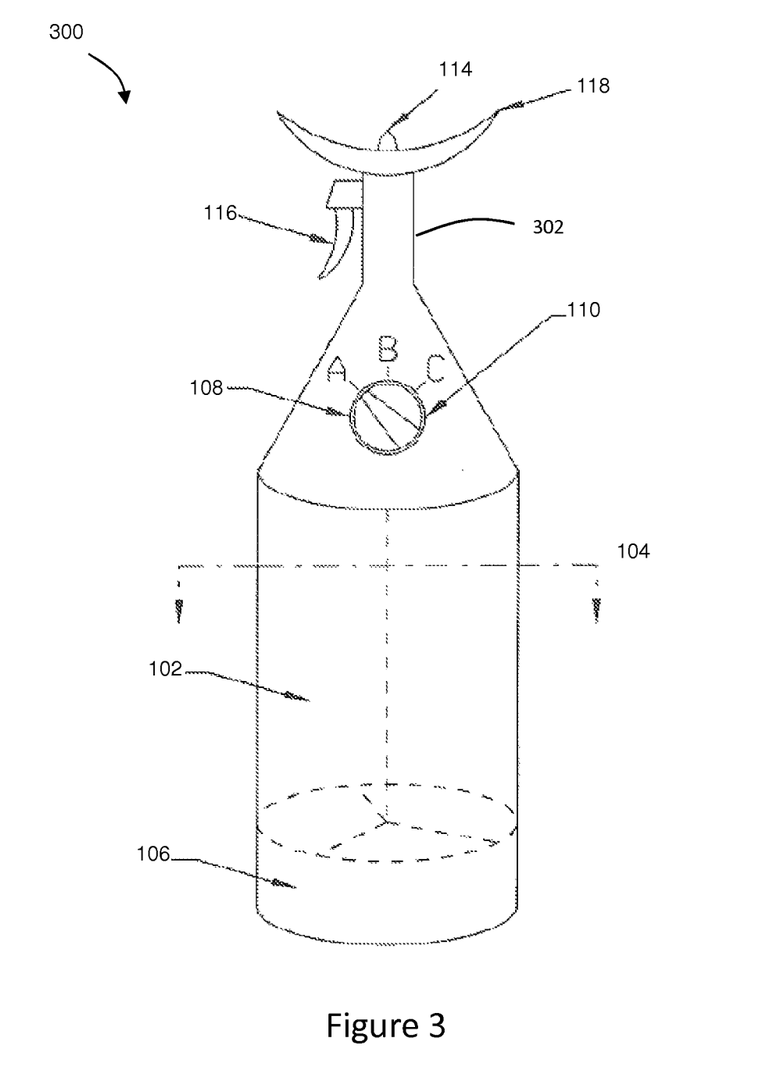
FIG. 3 illustrates a front view of a wound injector with a straight nozzle.

FIG. 2 illustrates another embodiment of a wound injector 200 where the flexible hose 112 is replaced by an about 90 degree nozzle 202. The nozzle 202 does not have to be oriented at 90 degrees. Instead, the wound injector may be configured to have the nozzle fixed at any angle or it may be configured to be adjustable by the user to a plurality of angles. For example, FIG. 3 illustrates an alternative embodiment of a wound injector 300 with a straight nozzle 302. The nozzle may move freely between ranges of angles, or it may be adjusted to one of predetermined positions.

Figure 4:
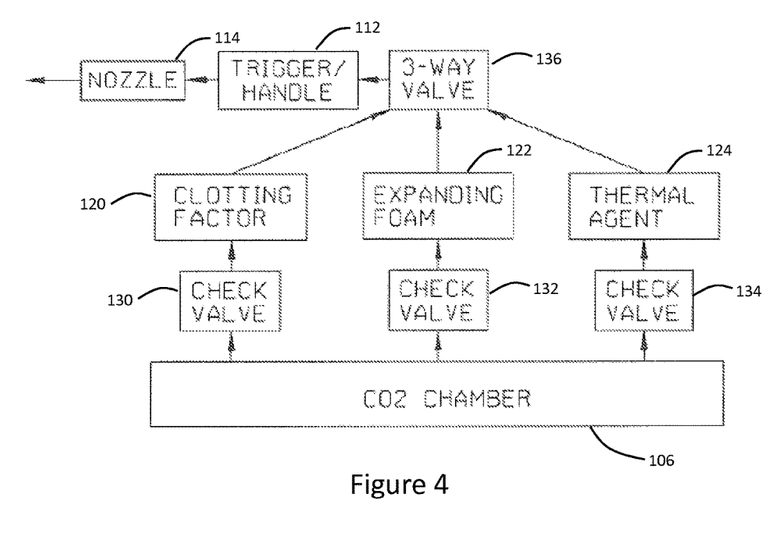
FIG. 4 illustrates a schematic diagram of the wound injectors from FIGS. 2 and 3.

FIG. 4 illustrates a schematic diagram for wound injector 200 and 300, where the three-way valve 136 connects directly to the nozzle 114 without flexible hose 112. As noted above, the nozzle may be configured to have its angle of orientation adjusted freely within a range of angles, or adjusted to one of a set of predetermined positions.

Figure 5:
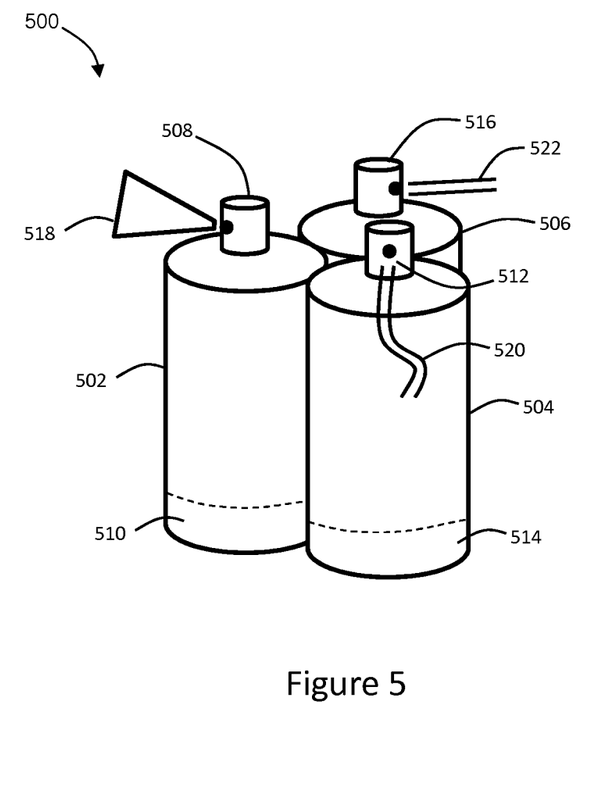
FIG. 5 illustrates a front view of a wound injector that includes three containers.

FIG. 5 illustrates an embodiment of a wound injector 500 that includes three separate containers for each of the active ingredients. A first container 502 houses the clotting factor, a second container 504 houses the expandable material, and a third container 506 houses the thermal agent. Wound injector 500 differs from other wound injector embodiments in that each container functions independently of each other, and thus no three-way valve is necessary for the illustrative embodiment. Each container includes its own actuator and its own propellant chamber. The first container 502 includes first actuator 508 and first propellant chamber 510 for dispensing the clotting factor. Similarly, the second container 504 includes second actuator 512 and second propellant chamber 514, and the third container includes third actuator 516 and third propellant chamber (not shown).

The containers 502, 504, and 506 may be fastened together with a fastener. Alternatively, and adhesive may be used to join the containers. While the containers 502-506 are illustrated as being substantially cylindrical shaped, alternative shapes may also be used. The various containers 502-506 of the wound injector need not be the same size and shape. For instance, if it is determined that a larger container is needed for the expandable material, then the second container 504 can be larger, while the first and third containers 502 and 506 may be smaller.

Each container may also use a different type of actuator with differently shaped and sized nozzles. Different diffusers may also be used for the different actuators. FIG. 5 illustrates the use of different diffusers for the various containers 502-506. Specifically, a substantially cone-shaped diffuser 518, a flexible tube 520, and a rigid tube 522 are illustrated as being used with actuators 508, 512, and 516.

Embodiments of the wound injector as described herein enable the stopping and slow-down of bleeding of a wound. The active ingredients of the wound injector may be applied in arbitrary order, and may be applied numerous times as necessary. For instance, the expandable material may be applied first, and once pressure is being applied to the wound, the clotting factor and the thermal agent may be applied to the entry and/or exit points of the wound.

Embodiments enable the treatment of a wide variety of wounds. For example, the wound injector can be used for a wound in an extremity. If a wound, such as a gunshot, is experienced in an extremity, then the wound injector may first be used to apply the clotting factor to the wound. Following the application of the clotting factor, the expandable material may be applied directly to the wound. The expandable material may be applied by positioning the nozzle adjacent to the wound or inside of the wound cavity. The expandable material may then be slowly dispersed to fill the wound cavity and thus exert pressure against the wound. As noted above, a sleeve may also be inserted into the wound, and once in place, the sleeve can be filled with the expandable material. Finally, the thermal agent is applied to the wound.

The wound injector may also be used to treat, for example, a wound in the neck or torso. The clotting factor may be applied first. Depending on the actual conditions of the neck or torso wound, the expandable material can be applied at the front of the wound and at the back of the wound, without applying any expandable material to the middle of the wound. The thermal agent may then be applied to the front of the wound and the back of the wound, without applying the thermal agent to the middle of the wound.

As yet another example, the wound injector may be used to treat a wound experienced in the cranial area. The clotting factor may be applied first to stop cerebral bleeding. When treating wounds in delicate areas, the clotting factor may be delivered at a low pressure to avoid further damage to the wound. Depending on the severity of the wound and the wound conditions, the expandable material may or may not be used to avoid damaging the cranial area. Finally, the thermal agent may be applied to minimize swelling of the brain.

The wound injector may include a diffuser attached to the at least one nozzle. The diffuser may be substantially cone-shaped diffuser, a rigid tube diffuser, and a flexible tube diffuser. Embodiments may also include cover adjacent to and partially surrounding the at least one nozzle.

It is to be understood that the detailed description of illustrative embodiments are provided for illustrative purposes. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A wound injector apparatus comprising:
   a clotting factor housed in a clotting factor chamber;
   an expandable material housed in an expandable material chamber;
   a thermal agent housed in a thermal agent chamber;
   at least one nozzle configured to discharge the clotting factor, the expandable material, and the thermal agent;
   a propellant chamber; and
   a propellant housed in the first propellant chamber.

2. The wound injector apparatus of claim 1, wherein the propellant chamber is divided into a first propellant chamber, a second propellant chamber, and a third propellant chamber, the propellant including:
   a first propellant housed in the first propellant chamber, wherein the first propellant is associated with the clotting factor chamber;
   a second propellant housed in the second propellant chamber, wherein the second propellant is associated with the expandable material chamber; and
   a third propellant housed in the third propellant chamber, wherein the third propellant is associated with the thermal agent chamber.

3. The wound injector apparatus of claim 2, further comprising a three-way valve controlling discharge from the clotting factor chamber, the expandable material chamber, and the thermal agent chamber.

4. The wound injector apparatus of claim 3 further comprising a selector switch for controlling the three-way valve.

5. The wound injector apparatus of claim 2, further comprising a selector switch for controlling discharge from the clotting factor chamber, the expandable material chamber, and the thermal agent chamber.

6. The wound injector apparatus of claim 2, wherein the at least one nozzle includes a first nozzle, a second nozzle, and a third nozzle, and wherein the wound injector apparatus further comprises:
   a first container including the clotting factor chamber housing the clotting factor, the first propellant chamber housing the first propellant, and the first nozzle for discharging the clotting factor;
   a second container including the expandable material chamber housing the expandable material, the second propellant chamber housing the second propellant, and the second nozzle for discharging the expandable material; and
   a third container including the thermal agent chamber housing the thermal agent, the third propellant chamber housing the third propellant, and the third nozzle for discharging the thermal agent.

7. The wound injector apparatus of claim 6 further comprising a fastener connecting the first container, the second container, and the third container.

8. The wound injector apparatus of claim 6, wherein an adhesive connects the first container, the second container, and the third container.

9. The wound injector apparatus of claim 1, wherein the propellant includes at least one of oxygen ($O_2$), carbon dioxide ($CO_2$), and nitrogen ($N_2$).

10. The wound injector apparatus of claim 1, further comprising a flexible hose connecting the one or more of the clotting factor chamber, the expandable material chamber, and the thermal agent chamber to the at least one nozzle.

11. The wound injector apparatus of claim 1, wherein the clotting factor includes at least one of thrombin, prothrombin, vitamin K, an adsorbent chemical, a hemostatic agent, and fibrin glue.

12. The wound injector apparatus of claim 1, further comprising a sleeve that is configured to apply direct pressure to a wound when filled with the expandable material.

13. The wound injector apparatus of claim 12, wherein the sleeve is composed of an elastomeric material.

14. The wound injector apparatus of claim 1, wherein the expandable material is bio-compatible, and as the expandable material cures the expandable material hardens.

15. The wound injector apparatus of claim 1, wherein the thermal agent includes at least one of oxygen ($O_2$), carbon dioxide ($CO_2$), and nitrogen ($N_2$).

16. The wound injector apparatus of claim 1, further comprising an indicator configured to indicate a remaining amount of at least one of the clotting factor, the expandable material, and the thermal agent.

17. The wound injector apparatus as recited in claim 1, wherein the at least one nozzle includes a first nozzle for discharging the clotting factor, a second nozzle for discharging the expandable material, and a third nozzle for discharging the thermal agent.

18. The wound injector apparatus of claim 1, further comprising a diffuser attached to the at least one nozzle.

* * * * *